United States Patent [19]

Mui et al.

[11] 4,044,037

[45] Aug. 23, 1977

[54] SULFUR CONTAINING SILANE COUPLING AGENTS

[75] Inventors: Jeffrey Y. P. Mui, Marietta, Ohio; Arthur N. Pines, Katonah, N.Y.

[73] Assignee: Union Carbide Corporation, New York, N.Y.

[21] Appl. No.: 536,207

[22] Filed: Dec. 24, 1974

[51] Int. Cl.² .......................... C07F 7/08; C07F 7/18
[52] U.S. Cl. ...................... 260/448.2 N; 260/448.8 R
[58] Field of Search ................. 260/448.2 N, 448.8 R

[56] References Cited

U.S. PATENT DOCUMENTS

| | | | |
|---|---|---|---|
| 2,719,165 | 9/1955 | Cooper | 260/448.2 N |
| 3,329,726 | 7/1967 | Landis et al. | 260/448.8 R X |
| 3,465,015 | 9/1969 | Speier | 260/448.2 N |
| 3,768,537 | 10/1973 | Hess et al. | 260/448.8 R X |
| 3,842,111 | 10/1974 | Meye-Simon et al. | 260/448.2 N X |
| 3,873,489 | 3/1975 | Thurn et al. | 260/448.2 N X |

FOREIGN PATENT DOCUMENTS

| | | | |
|---|---|---|---|
| 2,141,159 | 3/1973 | Germany | 260/448.2 N UX |
| 791,609 | 3/1958 | United Kingdom | 260/448.2 N UX |

*Primary Examiner*—Paul F. Shaver
*Attorney, Agent, or Firm*—Reynold J. Finnegan

[57] ABSTRACT

Polysulfide aryl silanes, mercapto aryl silanes, the hydrolyzates and condensates thereof, a process for the manufacture of said silanes, and their use as coupling agents in vulcanized rubber compounds.

17 Claims, No Drawings

SULFUR CONTAINING SILANE COUPLING AGENTS

BACKGROUND OF THE INVENTION

This invention relates to novel polysulfide aryl silanes and to novel mercapto aryl silanes, as well as to a novel process for their manufacture and their use as coupling agents in vulcanized rubber compounds.

Certain polysulfide alkyl silanes and certain mercapto alkyl silanes are known in the art as seen for example by German Pat. Nos. 1,000,817 and 2,141,159 and U.S. Pat. No. 2,719,165. However, the prior art has not been found to teach the novel polysulfide aryl silanes and novel mercapto aryl silanes of this invention.

SUMMARY OF THE INVENTION

Thus, it is an object of this invention to provide polysulfide aryl silanes, hydrolyzates and condensates thereof, and a novel process for their manufacture. Another object of this invention is to provide mercapto aryl silanes, hydrolyzates and condensates thereof. Still another object of this invention is to provide vulcanized rubber compounds as well as inorganic mineral fillers treated with said silanes and the hydrolyzates and condensates thereof. Other objects and advantages of this invention will become readily apparent from the following description and appended claims.

More specifically the polysulfide aryl silanes encompassed by this invention include those silanes having the average formula

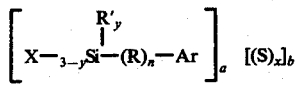

wherein X represents a hydrolyzable group selected from the class consisting of halogen, alkoxy and acyloxy radicals; wherein R' represents an alkyl radical containing from 1 to 4 carbon atoms; wherein $y$ has a value of from 0 to 2 inclusive; wherein R represents a divalent bridging group selected from the class consisting of alkylene and alkyleneoxy radicals containing from 1 to 7 carbon atoms; wherein $n$ has a value of 0 or 1; wherein Ar represents an aryl radical containing from 6 to 12 carbon atoms; wherein $(S)_x$ represents a divalent polysulfide radical each free valence thereof being directly bonded to an aromatic carbon atom of an Ar radical whereby each Ar radical is bonded to another Ar radical through a $(S)_x$ radical; wherein $x$ has a value of from 2 to 6; wherein $a$ has a value of at least 2; wherein $b$ has a value of at least 1; and wherein the ratio of $a$ to $b$ is a value of not more than 2. In addition this invention encompasses the hydrolyzates and condensates of said polysulfide aryl silanes.

Another aspect of this invention relates to a sulfuration process for producing said polysulfide aryl silanes which comprises sulfurating an aryl halo silane with sulfur monochloride.

Still another aspect of this invention relates to mercapto aryl silanes which include those silanes having the average formula

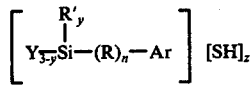

wherein R, R', Ar, $y$, and $n$ are the same as defined above, wherein [SH] represents a monovalent mercapto radical which is directly bonded to an aromatic carbon atoms of Ar; wherein $z$ has a value from 1 to 5, preferably 1 to 3 and wherein Y represents a hydrolyzable group selected from the class consisting of alkoxy and acyloxy radicals. In addition, this invention encompasses the hydrolyzates and condensates of said mercapto aryl silanes.

Yet another aspect of this invention relates to vulcanized rubber compounds in which the polysulfide aryl silanes, the mercapto aryl silanes, and the hydrolyzates and condensates of said silanes have been employed as coupling agents as well as to inorganic mineral fillers treated with said silanes, and the hydrolyzates and condensates thereof.

DESCRIPTION OF THE PREFERRED EMBODIMENTS

Illustrative hydrolyzable groups that may be represented by X in the above formula include halogen atoms, e.g. chlorine, bromine, and the like, especially chlorine; alkoxy radicals containing from 1 to 4 carbon atoms such as methoxy, ethoxy, propoxy, and the like; and acyloxy radicals containing from 1 to 4 carbon atoms such as acetoxy, and the like. Preferably X represents a hydrolyzable group selected from the class consisting of chlorine, methoxy and ethoxy radicals.

Illustrative hydrolyzable groups that may be represented by Y in the above formula include alkoxy radicals containing from 1 to 4 carbon atoms such as methoxy, ethoxy, propoxy, and the like; and acyloxy radicals containing from 1 to 4 carbon atoms such as acetoxy, and the like. Preferably Y represents a hydrolyzable group selected from the class consisting of methoxy and ethoxy radicals.

Illustrative alkyl radicals that may be represented by R' in the above formulas include methyl, ethyl, and the like, especiallly methyl.

Illustrative divalent bridging groups that may be represented by R in the above formulas include divalent alkylene radicals such as $-CH_2-$, $-C_2H_4-$, $-C_3H_6-$, $-C_4H_8-$, and the like and divalent alkyleneoxy radicals wherein the oxygen atom is bonded directly to Ar such as $-C_2H_4O-$, $-C_3H_6O-$ and the like. Of course, it is to be understood that said divalent bridging groups can be straight or branch chain radicals. Preferably R is an alkylene radical containing from 2 to 4 carbon atoms, especially $-C_2H_4-$

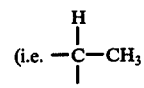

and/or $-CH_2CH_2-$).

Illustrative aryl radicals that may be represented by Ar in the above formulas which are directly bonded to the polysulfide or mercapto radicals of said formulas include, phenyl, naphthyl, alkyl substituted phenyl radicals wherein said alkyl radicals contain from 1 to 4 carbon atoms such as tolyl, xylyl, and the like, and alkoxy substituted phenyl radicals wherein the alkoxy radicals contain from 1 to 4 carbon atoms such as methoxyphenyl, ethoxyphenyl, propoxyphenyl and the like. Preferably Ar represents an aryl radical selected from the class consisting of phenyl, tolyl, and xylyl.

Moreover, the upper limits of the values of a and b in the above formulas must correspond to the ratio of a to b which is a value of not more than 2. In general, said ratio may range from 0.4 to 2 and preferably from 0.6 to 2. More preferably, a is 2 and b is 1. Of course, it is obvious as explained more fully below, that the value of z in the above silane mercaptan formula depends on the value of b in the above polysulfide silane formula, In addition, among the more preferred silanes of this invention represented by the above formulas are those wherein y has a value of 0 and x has an average value of from 2 to 4.

The process for preparing the above defined polysulfide aryl silanes of this invention comprises sulfurating an arylhalosilane to produce a polysulfide aryl halo silane product and then converting said silane product to its corresponding alkoxy- or acyloxy-containing polysulfide aryl silane compound.

More specifically, the polysulfide aryl halo-containing silane compounds of this invention having the average formula $$\left[\begin{array}{c} R'_y \\ | \\ Hal_{\overline{3-y}}Si-(R)_n Ar \end{array}\right]_a [(S)_x]_b$$

wherein Hal represents a halogen atom such as chlorine, bromine, and the like, especially chlorine, and wherein R, R', Ar, y, n, (S)$_x$ a, b and the ratio of a to b are the same as defined above can be conveniently prepared by a process comprising reacting (a) an arylhalosilane having the formula

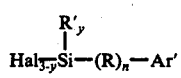

wherein Hal, R, R', y and n are the same as defined above and wherein Ar' represents a monovalent aryl radical containing from 6 to 12 carbon atoms with (b) sulfur monochloride and maintaining the reaction until hydrogen chloride gas evolution has essentially ceased.

Illustrative monovalent aryl radicals that may be represented by Ar' above include phenyl, naphthyl, alkyl substituted phenyl radicals wherein said alkyl radical contains from 1 to 4 carbon atoms such as tolyl, xylyl, and the like, and alkoxy substituted phenyl radicals wherein the alkoxy radicals contain from 1 to 4 carbon atoms such as methoxyphenyl, ethoxyphenyl, propoxyphenyl and the like. Preferably Ar' represents a monovalent aryl radical selected from the class consisting of phenyl, tolyl and xylyl.

Illustrative of some of the arylhalosilane starting materials useful in the novel sulfuration process of the instant invention include phenyltrichlorosilane, tolyltrichlorosilane, xylyltrichlorosilane, propylphenyltrichlorosilane, naphthyltrichlorosilane, tolylmethyltribromosilane, phenylethyltrichlorosilane, tolylethyltrichlorosilane, phenylethyldichloromethylsilane, methoxyphenyltrichlorosilane, phenyloxypropyltrichlorosilane, xylyloxypropyltrichlorosilane and the like. The most preferred materials are phenyltrichlorosilane

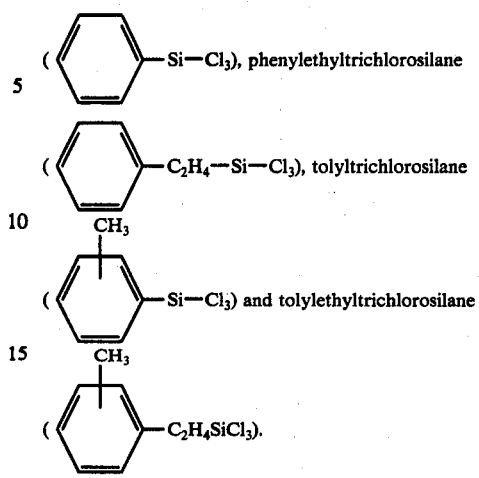

Of course, it is to be understood that in addition to employing only one type of arylhalosilane starting material at a time in the sulfuration process of this invention, mixtures of two or more different types of arylhalosilane starting materials can be employed if desired. It is to be also understood that while said arylhalosilanes can be discrete silane species, halosilanes containing an alkyl-substituted aryl radical are usually mixtures of various discrete isomer species due in part to the fact that the alkyl-substituted aryl compounds used to produce the corresponding arylhalosilane starting materials are themselves usually isomeric mixtures. Likewise the production of arylhalosilanes wherein the silicon atom is bonded to the aryl group through a divalent bridging group such as an alkylene radical also usually leads to isomeric mixtures due to the fact that the silicon atom can be bonded to different carbon atoms of said bridging group. Accordingly it is to be understood that the average formulas representing the novel polysulfide aryl silanes and novel mercapto aryl silanes of this invention encompass discrete silane species and isomeric silane mixtures for the same reasons.

Said arylhalosilane starting materials and/or methods for their preparation are well known in the art. For example, the arylhalosilanes can easily be prepared by conventional catalyzed reactions such as Friedel-Crafts substitution of an SiH bond with an aromatic compound or by the conventional platinum (e.g. chloroplatinic acid) catalyzed hydrosilation process of SiH with an olefinic substituted aromatic compound. Thus the process merely comprises producing the desired arylhalosilanes by reacting the aryl compound with the hydrohalosilane compound that corresponds to the arylhalosilane product desired as illustrated for instance by the following exemplative equations

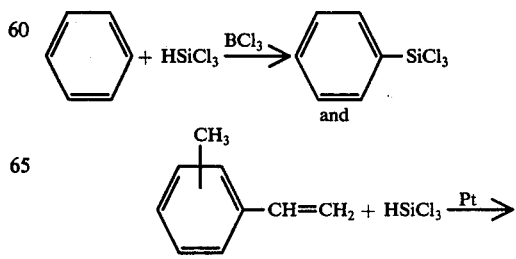

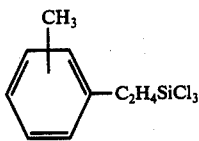

The sulfur monochloride reactant employed in the instant invention is a known compound and is represented by the formula $S_2Cl_2$. Moreover, the sulfuration process of the instant invention can be operated batchwise or continuously and with or without the use of an inert solvent. When employed the preferred solvents are chlorinated hydrocarbons, such as $CCl_4$, $C_2H_4Cl_2$, and the like, or saturated hydrocarbons, such as cyclohexane, heptane, and the like. Other solvents include acrylonitrile, carbon disulfide, ethers, and in cases of highly reactive arylhalosilanes, such as xylylethyltrichlorosilane, tolylethyltrichlorosilane, low reactive aromatics such as benzene and toluene. Of course, the amount of solvent used can be broadly varied to fit special situations as desired.

The sulfuration process of the instant invention involves reacting at least a stoichiometric amount of arylhalosilane and sulfur monochloride i.e. at least one mole of sulfur monochloride for every two moles of arylhalosilane employed. When less than a stoichiometric amount of sulfur monochloride is employed there will be unsulfurated arylhalosilane, which is left unrecovered functions as an inert diluent, and which can lower the yield and purity of the desired polysulfide silane product. Thus, while not wishing to be bound to any preconceived or definite reaction mechanism, when an essentially stoichiometric amount of one mole of sulfur monochloride is used for sulfurating two moles of an arylhalosilane starting material a sulfurated product is obtained which is comprised essentially of one polysulfide $(S)_x$ bridging group linking the two aromatic rings. This reaction is stepwise illustrated by the following exemplative idealized equations:

and C below). In this respect, it is believed that the reaction parallels the course of a conventional Friedel-Crafts alkylation of an aromatic compound with an excess amount of alkyl halide relative to the aromatic, the resultant product comprising of multiple alkyl groups attached to the aromatic ring. This reaction is stepwise illustrated by the further reaction of Compound A with the excess sulfur monochloride as shown by the following idealized equations:

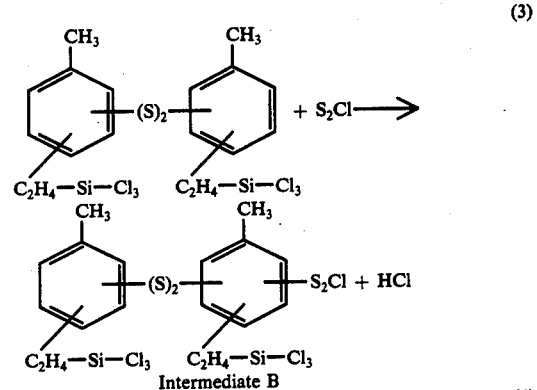

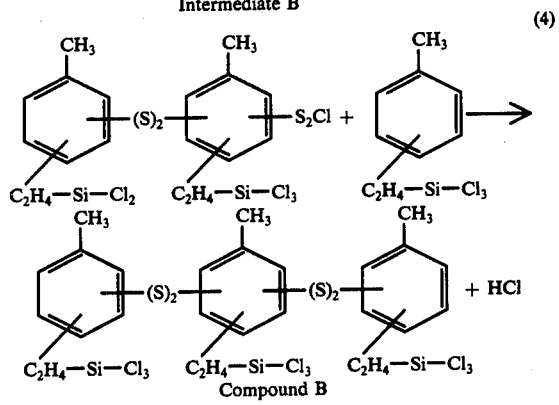

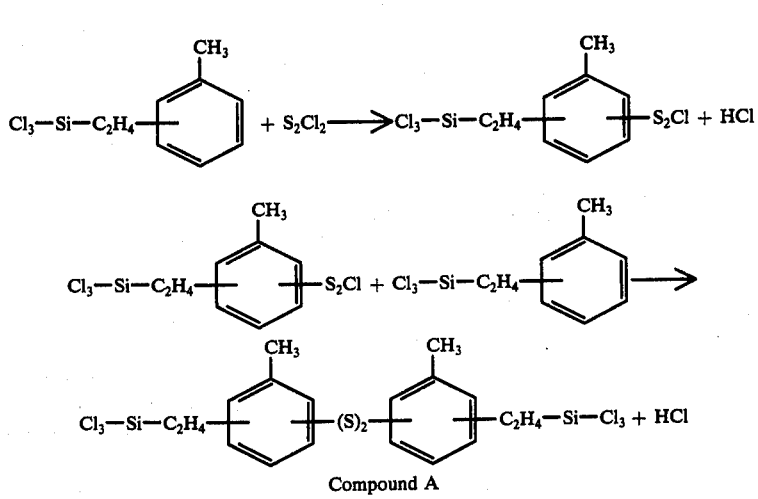

Larger excess amounts of sulfur monochloride may also be reacted with the arylhalosilanes to give more highly substituted products (i.e. more than one polysulfide bridge per aromatic ring as illustrated by Compounds B and in a similar manner the reaction product of even a further excess amount of sulfur monochloride may give a resultant sulfurated product illustrated by Compound C below:

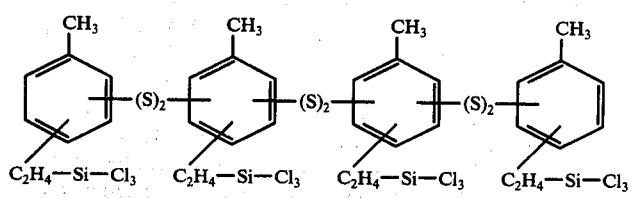

and so on and so forth until the most maximum sulfurated reaction product possible is obtained. Thus, it is obvious that depending upon the amount of sulfur monochloride employed, polysulfide aryl silanes may be obtained wherein each Ar group in the above generic formula representing the novel polysulfide aryl silanes of this invention contains at least one aromatic carbon atom that is directly bonded to a polysulfide bridging group represented by $(S)_x$ above which, in turn, is directly bonded to an aromatic carbon atom of another Ar group; the most simple polysulfide aryl silane compound of course being a diaryl compound having a single polysulfide bridging group e.g. —Ar—$(S)_x$—Ar—, the more complex compounds containing one or more aromatic rings having one or more polysulfide bridging groups directly bonded to the same aromatic ring, e.g. —Ar—$(S)_x$—Ar—$(S)_x$—AR—$(S)_x$—Ar—$(S)_x$—Ar—$(S)_x$—Ar, and the like. Of course, it is to be understood that it may also be possible that the reaction products of the instant novel sulfuration process of this invention may include some cyclic polysulfide aryl silane compounds, i.e., compounds in which two aromatic rings are bonded together through two polysulfide bridging groups, e.g.

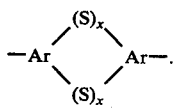

Even though in formula compounds A, B and C above, the polysulfide bridging groups are listed as disulfides they may be polysulfides containing from 2 to 6 carbon atoms for as is well known to one skilled in the art, sulfur monochloride is readily prone to disproportionate at elevated temperatures in the presence of minor amounts of metal or metal halide impurities such as $FeCl_3$, and the like, to form $S_3Cl_2$, $S_4Cl_2$ and smaller amounts of $S_5Cl_2$ and the like which can also sulfurate the arylhalosilanes as depicted by $(S)_x$ in the formulas above.

Accordingly, it is to be understood that the formulas representing the novel polysulfide aryl silane and novel silane mercaptan compounds of this invention are average formulas encompassing not only discrete silane species and isomeric mixtures for the reasons explained above, but also encompass mixtures that may be caused by the amount of sulfur monochloride employed in the sulfuration process of the instant invention and the fact that the polysulfide bridging groups have the opportunity to bond at a multiple of available aromatic proton sites present in the original aryl halo silane starting material. Thus, in the generic formula for the novel polysulfide aryl silanes of this invention when $a$ equals 2 and $b$ equals 1, the average formula represents silanes of the type of Compound A above and when $b$ equals 2 or more the average formula represents silanes of the type of Compounds B and C above. This is not to say, however, that smaller amounts of silanes of either type or even of the above cyclic type are in actuality definitely precluded from the average silane reaction product of anyone specific type of formula.

Thus, the sulfuration process of the instant invention involves employing at least a stoichiometric amount of sulfur monochloride i.e., at least one mole of sulfur monochloride for every two moles of arylhalosilane compound used. While the upper limit of the amount of sulfur monochloride employed is obviously not critical, amounts in the range of about at least one mole to about four moles of sulfur monochloride for every two moles of arylhalosilane should be sufficient for most purposes. In general it is considered that sulfuration products having the average formula wherein $a$ equals 2 and $b$ equals 1 (e.g. silanes like Compound A above) are best favored by employing from at least 1 to about 1.5 moles of sulfur monochloride for every two moles of arylhalosilane used, while sulfuration products having the average formula wherein $b$ equals 2 or more (e.g. silanes like Compounds B and C above) are best favored by employing from about 2 to about 4 moles or more of sulfur monochloride for every two moles of arylhalosilane used.

While it is generally preferred to carry out the sulfuration process in the presence of a catalyst the use of such may not be absolutely necessary in every instance. When employed it is preferred to utilize a Lewis acid catalyst and any such catalyst may be employed. Such catalysts are well known compounds and include such acid halides as $BeCl_2$, $CdCl_2$, $ZnCl_2$, $BF_3$, $BCl_3$, $BBr_3$, $GaCl_3$, $GaBr_3$, $TiCl_4$, $ZrCl_4$, $SnCl_4$, $SbCl_5$, $BiCl_3$, $FeCl_3$, $UCl_4$, and the like. Of course it is to be understood that the preferred catalyst employed can depend upon such obvious factors as the reactants involved, the rate of reaction desired, and the like, as well as the desired end use of the sulfurated product since the catalyst is normally left to remain in said product. Moreover it is to be further understood that not every catalyst may be suitable for use with every arylhalosilane starting material. The most preferred catalysts are $FeCl_3$ and $TiCl_4$. Obviously, the amount of catalyst employed need only be a catalytic amount. Generallly amounts ranging from about 0.5 to about 10 percent by weight based on the amount of sulfur monochloride employed should be sufficient with best results generally being obtained with the smallest operable amounts of catalyst.

The reaction temperature of the sulfuration process of the instant invention is not known to be critical and may be held at any temperature at which a reaction occurs as witnessed by the evolution of hydrogen chloride gas and which is below the temperature at which decomposition may occur. While the preferred reaction temperature will depend upon such obvious factors as the reactants, activating solvents and catalyst employed, it is generally preferred to operate the reaction at a temperature at which a steady stream of hydrogen chloride gas evolution occurs. In general the reaction temperature may normally range from about −20° C. to 150° C. and more preferably from about 50° C. to about 125° C.

The reaction time of the sulfuration process of the instant invention is also of course merely a function of such obvious factors as the amount and type of reactants and catalyst employed, the reaction temperature, etc. In general, it is preferred that the reaction be maintained until all hydrogen chloride gas evolution has essentially ceased. The expression "essentially ceased" as employed herein means that for all practical purposes the reaction has been completed as witnessed by the evolution of only periodic bubbles of hydrogen chloride gas being driven off as adverse to a steady stream of hydrogen chloride gas evolution. This also signifies that all of the sulfur monochloride has been essentially (at least about 90%) consumed.

The above defined polysulfide aryl halo-containing silanes of this invention may be recovered and if desired purified by any conventional method and employed as coupling agents themselves as more fully discussed below. However, it is generally preferred to employ said polysulfide aryl halocontaining silanes as the starting materials for the preparation of the polysulfide aryl alkoxy- and acyloxy-containing silanes of this invention.

The polysulfide aryl alkoxy- or acyloxy-containing silanes of this invention can be easily prepared by any conventional known method of esterifying a corresponding halocontaining silane compound. Thus, the polysulfide aryl alkoxy- or acyloxy-containing silanes of this invention which may be represented by the average formula

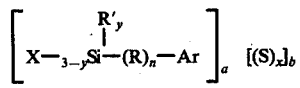

wherein R, R', Ar, $y$, $n$ and $(S)_x$ are the same as defined above are conveniently preparing by reacting a polysulfide aryl halo-containing silane having the average formula

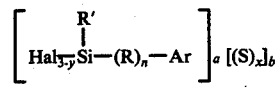

wherein Hal, R, R', Ar, $y$, $n$ and $(S)_x$ are the same as defined above with an alcohol or acyl compound having from 1 to 4 carbon atoms. The alkoxy or acyloxy radical represented by X above will of course correspond to the particular alcohol or acyl compound employed in the esterification process. Illustrative examples of such alcohols include methanol, ethanol, propanol, butanol, and the like, while illustrative acyl compounds include acetic anhydride, and the like. Said type of esterification process is well known in the silicon art and may be represented by the following illustrative unbalanced equation.

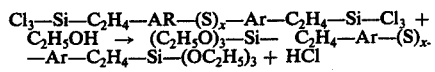

wherein Ar and $x$ are the same as defined above. The particular reaction conditions of the esterification process are well within the knowledge of one skilled in the art, while the preferred conditions can be determined by routine experimentation and will of course merely depend upon such obvious factors as the amount and nature of the reactants involved, and the like. In theory, the esterification process is a stoichiometric reaction involving the use of one mole of alcohol or acyl compound for each mole of silicon-halide bond in the starting silane to be reacted. More perferably an excess amount of the alcohol or acyl compound is employed and such excess amounts may range from about 10 to about 100% or higher above the theoretical stoichiometric amount of alcohol or acyl compound required to esterify all of the halo-silane bonds in the starting silane material. The esterification prociess is preferably an anhydrous reaction and may be conducted at atmospheric pressure or under vacuum pressures such as 100–300 mm Hg. and at temperatures ranging from about 20° C. to about 120° C., preferably from about 50° C. to about 110° C. Completion of the esterification process can be easily determined by titration of the reaction mixture to determine when it is free of residual silicon halide or of hydrogen halide by-product. The polysulfide aryl alkoxy- or acyloxy-containing silane product can be easily refined and recovered by any conventional method such as by neutralizing, washing, filtering, and distilling the final esterified product. For instance, while not absolutely necessary, if desired the esterified polysulfide reaction product can be neutralized with any conventional neutralizing agent such as $NaHCO_3$ or alkylene oxide to remove any residual acidity, and purified by stripping at 90°C–150° C. and less than 0.1 to 5 mm Hg. to remove unsulfurated aryl silane starting material, followed by filtration and then further heat treating the esterified reaction product to remove any residual volatiles that may be present.

The novel sulfuration process of the instant invention is indeed unique in that it provides an extremely economical method for producing various highly effective polysulfide and mercaptan coupling agents. Said process requires only a minimum amount of equipment, and the reactants and product of said process are very easy to handle since only liquids and gases are involved. Moreover, said process avoids the production of solid halide salt by-products thus eliminating the need for large amounts of solvent and separate filtration equipment to recover the desired product.

In addition to their use as coupling agents as more fully described below, the polysulfide aryl alkoxy- and acyloxy-containing silanes of this invention can be employed as starting materials for the preparation of the corresponding aryl alkoxy: and acyloxy-containing silane mercaptans of this invention. Said mercaptans may be represented as having the average formula

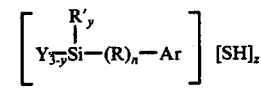

wherein Y, R, R', Ar, $y$, $n$, [SH] and $z$ are the same as defined above.

Said novel silane mercaptans of this invention can be easily prepared by any conventional known method of reductive thiolation or hydrogenation of a corresponding polysulfide compound. Said methods are well known in the art and may be represented by the following illustrative unbalanced equation

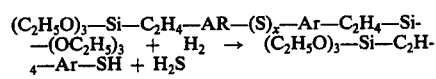

wherein Ar and $x$ are the same as defined above. The particular reaction conditions of the hydrogenation process are well within the knowledge of one skilled in the art, while the preferred conditions can be determined by routine experimentation and will of course merely depend upon such obvious factors as the amount and nature of the reactants involved, and the like. Of course, it is obvious that the desired aryl silane mercaptan product will be dictated by the particular corresponding polysulfide aryl silane starting material employed. For example, an aryl silane starting material containing one polysulfide bridging group (e.g. —Ar—$(S)_x$—Ar—) will yield a silane containing one mercapto group (e.g. —Ar—SH); an aryl silane starting material containing two polysulfide bridging groups attached to the same aryl ring (e.g, —Ar—$(S)_x$—Ar—$(S)_x$Ar—$(S)_x$—Ar—) will yield both a silane containing two mercapto groups (e.g, —Ar—$[SG]_2$) and a silane containing one mercapto group; and so forth depending on the number of polysulfide bridging groups attached to the same aryl ring in the aryl silane starting material. In theory the hydrogenation process is a stoichiometric reaction involving the use of one mole of hydrogen gas for each mole of polysulfide radical in the starting silane to be split. More preferably an excess amount of hydrogen is employed and such excess amounts may range form about 25% to about 200% or higher, above the theoretical stoichiometric amount of hydrogen required to split all of the polysulfide radicals in the starting silane material. The hydrogenation process is preferably conducted under anhydrous conditions and may be conducted at atmospheric pressure or super atmospheric pressures such as 50 to 5000 psig. and at temperatures ranging from about 75° C. to 250° C. Normally, a catalyst such as cobalt polysulfide or molybdenum sulfide, and the like is employed. Completion of the hydrogenation process can be easily determined by the absence of any further absorption of hydrogen gas into the reaction system. The aryl alkoxy- and acyloxy- containing silane mercaptan products can be easily recovered and purified by distillation or by any conventinal method such as those discussed above.

The hydrolyzates and condensates of the novel polysulfide aryl silanes and novel aryl silane mercaptan compounds of this invention can be prepared by the conventional known methods of hydrolysis and condensation. As is well known in the art, hydrolyzates represent the metathetical reaction products of water and corresponding hydrolyzable silanes, while condensates represent the siloxane products obtained upon condensation of the hydrolyzate reaction mixture. The hydrolyzates of the polysulfide aryl silanes and aryl silane mercaptan compounds of this invention can easily be obtained by mixing the desired silane or mixtures thereof to be hydrolyzed with water, while the condensates of the polysulfide aryl silanes and aryl silane mercaptan compounds of this invention can be equally easily obtained by condensation of said hydrolyzates of this invention. The amount of water employed is not critical and merely depends upon the degree of hydrolysis and condensation desired. Accordingly, it is to be understood, as employed herein the hydroylzates and condensates of this invention encompass in addition to completely hydrolyzed products and completely condensed products, partial hydrolyzates and partial condensate product mixtures obtained upon partial hydrolysis and partial condensation of the polysulfide aryl silanes and aryl silane mercaptan compounds of this invention.

Thus, it is obvious that the hydrolyzates of this invention encompass products wherein the hydrolyzable groups of the polysulfide aryl silanes and aryl silane mercaptan compounds of this invention have been at least partially hydrolyzed, for example, products wherein at least one of the X radicals (representing a halogen, alkoxy or acyloxy radical) in the above polysulfide aryl silane formula has been converted to a hydroxyl (HO—) radical, and products wherein at least one of the Y radicals (representing alkoxy or acyloxy radicals) in the above mercapto aryl silane formula has been converted to a hydroxyl (HO—) radical. Likewise it is obvious that the condensates of the polysulfide aryl silanes of this invention encompass siloxane products consisting essentially of siloxane units having the average formula

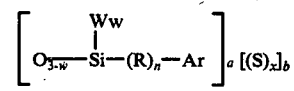

while the condensates of the aryl silane mercaptan compounds of this invention encompass siloxane products consisting essentially of siloxane units having the average formula

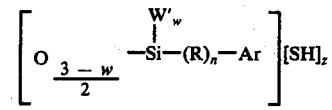

In the above siloxane unit formulas R, Ar, $n$, $(S)_x$, $a$, $b$, the ratio of $a$ to $b$ and $[SH]_z$ are the same as defined above; each W radical individually represents a member selected from the class consisting of an alkyl radical containing from 1 to 4 carbon atoms (i.e. the R' radical as defined above), hydroxy, halogen, alkoxy and acetoxy radicals; each W'0 radical individually represents a member selected from the class consisting of an alkyl radical containing from 1 to 4 carbon atoms (i.e. the R' radical as defined above), hydroxy, alkoxy and acetoxy radicals; and $w$ has an average value of 0 to 2, preferably 0.1 to 1.9. Of course, it is obvious that illustrative radicals represented by W and W' above are represented by X, Y and Hal as defined above, and that each W and W' in a particular siloxane condensate can be the same or different. These polymeric siloxanes include the trifunctional siloxanes, difunctional siloxanes and monofunctional siloxanes.

In addition, it is to be understood that the condensates of the polysulfide aryl silanes and aryl silane mercaptan compounds of this invention can be homopolymers or copolymers, said copolymers, of course, containing in addition to the above siloxane units one or more siloxane units having the average formula

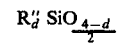

wherein R" is a radical selected from the group consisting of hydroxy, alkoxy, aryloxy, acyloxy and monovalent hydrocarbon radicals, $d$ has a value of 0 to 3 and need not be the same value throughout the same molecule, and R" can represent the same are different groups within the same molecule. Illustrative monovalent hydrocarbon radicals that R" can represent are alkyl groups such as methyl, ethyl, butyl and the like; aryl groups such as phenyl and the like; aralkyl such as phenylethyl and the like; and alkaryl such as tolyl and the like. The siloxane condensates include end-blocked linear polymeric siloxane oils, cyclic siloxanes, and resinous siloxanes containing the same or different substituted mono-, di- and trifunctional silicon atoms.

As pointed out above, the hydrolyzates of the polysulfide aryl silanes and aryl silane mercaptan compounds of this invention can be prepared by conventional hydrolysis methods such as by mixing the silane with water at 0° to 100° C., preferably about room temperature and maintaining the pH at about 2.5 to 9.5 preferably 4 to about 7. The condensates of the polysulfide aryl silanes and aryl silane mercaptan compounds of this invention can likewise be conventionally prepared by conventional condensation of the hydrolyzates or cohydrolysis and co-condensation of the silanes of this invention with other conventional hydrolyzable and/or condensible silanes such as those of the formula $R'''_rSiQ_{4-r}$, wherein $R'''$ is a monovalent hydrocarbon radical, r has a value of 0 to 4 and Q is a radical such as hydroxy, alkoxy, aryloxy, and acetoxy, e.g., ethyltrichlorosilane, dimethyldichlorosilane, phenyltrichlorosilane, methylphenyldichlorosilane, methyltriethoxysilane, dimethyldiethoxysilane, tetrachlorosilane, and the like. Condensation and co-condensation may be accelerated by the initiation of heat (heat to above 100° C.) and/or the use of conventional acidic or basic materials such as hydrochloric acid, sulfuric acid, amines and alkali metal hydroxides to render the hydrolyzate more acidic or basic. While a solvent is not absolutely necessary, a solvent may be employed during hydrolysis, if desired. Suitable solvents are, for example, isopropylether, diethylether and the like; toluene, benzene and the like; the diethers of ethylene glycol and polyethylene glycol and the like; and alcohols such as methanol, ethanol, isopropanol and the like. Recovery of a desired product may be obtained by any conventional method.

As pointed out above, this invention is also directed to novel vulcanized rubber compounds for mechanical rubber goods such as belting, motor mounts, tires, and the like. As is well known in the art, such vulcanized rubber compounds generally comprise a vulcanizable rubber polymer, a filler or pigment and a coupling agent that is capable of forming a connection or bond between the filler and rubber polymer. Thus, the coupling agent serves as a crosslinker that is chemically or physically bonded to both the filler and rubber polymer.

Accordingly, the present invention encompasses the use of the novel polysulfide aryl silane and novel aryl silane mercaptan compounds and the hydrolyzates and condensates of said silanes of the instant invention as coupling agents in any conventionally known vulcanized rubber compound that requires an inorganic mineral filler in the same manner that conventional coupling agents have been employed heretofore. Moreover, it has been discovered that improved physical properties may be imparted to the vulcanized rubber compounds when the polysulfide aryl silanes and/or aryl silane mercaptans of the instant invention are employed as coupling agents along with inorganic mineral fillers. Such improved properties may be many and varied depending upon the particular materials employed, however such effects are usually easily determinable and manifested in changes in the values of the vulcanized rubber product properties away from the values of the same properties displayed in the absence of said polysulfide aryl silane and/or aryl silane mercaptan coupling agents. For instance, the improved effects attributable to the instant invention may be seen in the vulcanized rubber product in terms of its resistance to deforming forces such as commonly expressed by tensile, compression and sheer moduli, its increased abrasion resistance and in decreased hysteresis losses in flexure and other such physical properties.

Indeed, it has been surprisingly discovered that polysulfide aryl silane coupling agents of this invention can be employed to help produce vulcanized mineral filled rubber compounds having excellent stress-strain characteristics, tear strength and reduced heat buildup during flexure, without unduly adversely affecting processing scorch safety, thus indicating that an excellent durable rubber article can be prepared without unduly sacrificing scorch safety. Likewise, it has been surprisingly found that aryl silane mercaptan coupling agents of this invention can be employed to help produce vulcanized mineral filled rubber compounds having excellent modulus values indicating that such rubber articles will possess excellent dynamic physical properties such as abrasion resistance, and the like.

Thus, another aspect of this invention relates to vulcanized rubber compounds comprising the reaction product of (a) a vulcanizable, non-pourable, unsaturated rubber polymer, (b) an inorganic mineral filler and (c) a coupling agent selected from the group consisting of polysulfide aryl silane compounds having the average formula

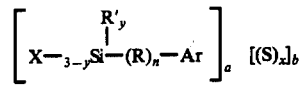

and the hydrolyzates and condensates thereof, and aryl silane mercaptan compounds having the average formula

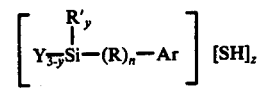

and the hydrolyzates and condensates thereof, wherein X,Y,R,R′, Ar, y, a, b, the ratio of a to b, n, $(S)_x$, and $[SH]_z$ are the same as defined above.

The vulcanizable, non-pourable, unsaturated rubber polymers employed in the novel vulcanized rubber compounds of this invention, as well as methods for their preparation are well known in the art. The term non-pourable as employed herein means that the vulcanizable rubber polymer is not pourable at about 25° C. Illustrative of such vulcanizable rubber polymers are natural rubber and synthetic rubber polymers as disclosed, e.g. in *The Elastomer Manual* (1972 Edition) published by International Institute of Synthetic Rubber Producers, Inc., Headquarters office at 45 Rockefeller Plaza, New York, New York 10020, such as styrene-butadiene rubber polymers, butadiene rubber polymers, ethylene-propylene rubber terpolymers, chloroprene rubber polymers, nitrile rubber polymers, bromo- and chloro- butyl rubber polymers, polyisoprene rubber polymers, and the like. The preferred vulcanizable, non-pourable unsaturated rubber polymers are the conventional sulfur vulcanizable rubber polymers such as natural rubber, styrene-butadiene rubber polymers, butadiene rubber polymers, and polyisoprene rubber polymers.

The inorganic mineral fillers (pigments) of the novel vulcanized rubber compound of this invention as well as methods for their manufacture are well known in the art and include e.g., any conventional inorganic mineral filler which is substantially reactive toward the coupling agents employed in the instant invention. Illustrative of such types of inorganic mineral fillers are the siliceous fillers such as hydrated precipitated silica, fumed silica, silica aerogels, silica xerogels; the metal silicates, such as aluminum silicate, calcium silicate, calcium metasilicate, magnesium silicate; the metal oxides such as aluminum oxide (including the hydrated versions), titanium dioxide, zinc oxide, zirconium oxide, inorganic fibers such as glass fibers, metal fibers; and the like. Of course, it is to be understood that such inorganic mineral fillers can be a naturally occurring mineral filler or a synthetically produced mineral filler. The preferred inorganic mineral fillers are siliceous and silicate materials, especially silica.

The function of a coupling agent to provide a strong chemical bridge between the filler and the rubber polymer employed is well known in the art. It is of course to be understood that for effective coupling action in a particular polymer-filler composite, it is necessary to select the appropriate coupling agent, i.e. one which is suitably reactive towards both the polymer component and the filler component for each particular polymer-filler composite considered. Thus, while there may be more than one appropriate coupling agent for a particular polymer-filler composite, a given coupling agent may not be appropriate for all polymer composites. However, the selection of the most preferred coupling agent for any particular polymer composite is well within routine experimentation. Of course, the novel coupling agents employable in the novel vulcanized rubber compounds of this invention have already been defined hereinabove along with their preferred embodiments.

The particular manner of compounding and vulcanizing the rubber compounds of this invention as well as the various amounts of ingredients employed is conventionally known and merely depends on the particular vulcanized rubber compound desired along with the ultimate end use for which it is to be employed, and such conventional steps as compounding, vulcanization, and the like may be conducted in the same known manner as heretofore employed for conventional vulcanized rubber compounds. For example, the novel coupling agents of this invention can be reacted with the filler prior to incorporating the filler into the rubber polymer batch. Said coupling agents can also be reacted with the rubber polymer prior to incorporation of the filler or they can be added to the rubber polymer batch together with the filler and various other additives during banbury mixing.

Preferably the polysulfide aryl silane and aryl silane mercaptan coupling agents of this invention are employed neat and are mixed with the filler and then added to the rubber polymer batch prior to the incorporation of the other conventional additives normally employed. However, if desired, the hydrolyzates and/or condensates of said silanes can be separately formed and then reacted with the filler prior to addition to the rubber polymer batch. Such separately formed hydrolyzates and condensates are preferably employed in the form of aqueous alcoholic compositions containing from about 0.01:20 parts by weight of water to about 99.99:80 parts by weight of alcohol solvent. In general the amount of coupling agent employed in the vulcanized rubber compounds of this invention will normally range from about 0.1 to about 20 parts by weight (preferably from about 1 to about 10 parts by weight) per 100 parts by weight of inorganic mineral filler employed although higher or lower amounts may be employed if desired. Of course, the amount of inorganic mineral filler employed merely depends on the desired end rubber product end use and may range from about 5 up to as high as 300 parts by weight or higher per 100 parts by weight of vulcanizable rubber polymer employed. The vulcanized rubber compound is normally vulcanized in the presence of conventional sulfur or peroxide curatives that are well known in the art. For example, a conventional sulfur curative may include per 100 parts by weight of vulcanizable rubber polymer from about 0.5 to 4 parts by weight of sulfur, about 2 to 5 parts by weight of zinc oxide, and about 0.2 to 3 parts by weight of accelerators (e.g. guanidine); while a conventional peroxide curative generally may include per 100 parts by weight of vulcanizable rubber polymer from about 1 to about 8 parts by weight of an organic peroxide e.g. dicumyl peroxide, $\alpha,\alpha'$-bis(t-butyl peroxy) diisopropylbenzene, and the like. The vulcanization procedure of a rubber polymer is well known in the art and in general may be conducted at temperatures ranging from 260° F to about 360° F. Of course, it is obvious that if desired the vulcanized rubber compounds of this invention may contain any of the conventionally additional ingredients such as extenders, carbon blacks, processing oils, plasticizers, antioxidants, lubricants, accelerators, retardants, coloring pigments and dyestuffs and the like, normally employed in conventional vulcanized rubber compounds and such is well within the knowledge of one skilled in the art.

Thus, yet another aspect of this invention relates to inorganic mineral fillers treated with a coupling agent selected from the group consisting of polysulfide aryl silane compounds having the average formula

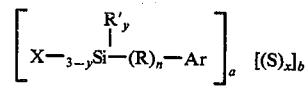

and the hydrolyzates and condensates thereof, and aryl silane mercaptan compounds having the average formula

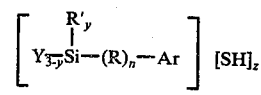

and the hydrolyzates and condensates thereof, wherein X, Y, R, R', Ar, y, a, b, n, (S)$_x$ and [SH]$_z$ are the same as defined above. Of course, illustrative inorganic mineral fillers, treatment conditions and the preferred embodiments of the novel treated inorganic mineral fillers of this invention are likewise the same as already herein defined above.

In addition to the above described utilities, the polysulfide aryl silanes, aryl silane mercaptan compounds, and the hydrolyzates and condensates thereof have numerous other utilities and can be employed e.g. as adhesives, protective coatings, and lubricants for metals, organic and inorganic materials such as glass, glass fibers, polyester fibers and the like, primers for rubber latex coatings, antioxidants, and as surface modifiers for fillers and pigments, and the like. Moreover, the above described treated inorganic mineral fillers of this invention, in addition to being employable in mineral filled elastomers, can also be employed in mineral filled plastic products.

The following examples are illustrative of the present invention and are not to be regarded as limitative. It is to be understood that all parts, percentages and proportions referred to herein and in the claims are by weight unless otherwise indicated and that the average polysulfide chlorosilane formulas are based on the calculated sulfur to silicon ratio found in the esterified polysulfide silane products.

EXAMPLE 1

About 826 grams (7.0 moles) of vinyl toluene (about a 40% meta-vinyl toluene and 60% para-vinyl toluene isomeric mixture) and about 0.5 grams of di-t-butyl-p-cresol were charged to a two liter three necked round bottom flask fitted with a magnetic stirrer, thermometer, dropping funnel and a reflux condenser bearing a nitrogen by-pass on the vent. While stirring the flask contents were heated to 90° C. and a sufficient amount of about a 2% solution of chloroplatinic acid catalyst dissolved in dimethylether of ethylene glycol to give about 25 parts by weight of platinum per million parts by weight of reactants was added. Then about 948.5 grams (7.0 moles) of trichlorosilane (HSiCl$_3$) were slowly and continuously added via the dropping funnel over a two-hour period while maintaining the reaction temperature at 120°-130° C. The crude reaction product mixture was then vacuum distilled through a Vigreaux column to give about 1622.5 grams (6.34 moles) of tolylethyltrichlorosilane product (91.4% conversion) which had a boiling point in the range of 70°-78° C/0.2 mm Hg. Nuclear magnetic resonance showed the tolylethyltrichlorosilane product

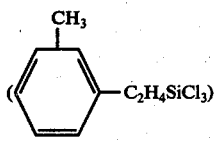

to be an isomeric mixture, about 52% of which had a silicon atom attached to the alpha carbon atom of the ethylene radical (i.e. the ethylene carbon atom which is attached directly to the tolylene radical) and about 48% of which had a silicon atom attached to the beta carbon atom of the ethylene radical (i.e. the ethylene carbon atom which is not attached directly to the tolylene radical).

EXAMPLE 2

About 468 grams (4.5 moles) of styrene and about 0.5 grams of di-t-butyl-p-cresol were charged to a one liter, three necked round bottom flask fitted with a magnetic stirrer, thermometer, dropping funnel and reflux condenser bearing a nitrogen by-pass on the vent. While stirring the flask contents were heated to 90° C, and a sufficient amount of about a 2% solution of chloroplatinic acid catalyst dissolved in dimethylether of ethylene glycok to give about 25 parts by weight of plantinum per million parts by weight of reactants was added. Then about 610 grams (4.5 moles) of trichlorosilane were slowly and continuously added via the dropping funnel over a one and one-half hour period while maintaining the reaction temperature at 90°-95° C. A vapor phase chromatogram on the reaction contents indicated there was an essentially complete conversion to product. The crude silane reaction product was then refined by a one plate distillation at 0.1 mm. pressure to yield about 1015 grams (4.24 moles) of phenylethyltrichlorosilane product

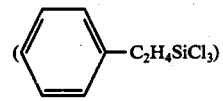

(94.5% conversion) which had a boiling point of about 63°-64° C./0.1 mm Hg.

EXAMPLE 3

About 253.5 grams (1.0 mole) of the tolylethyltrichlorosilane product of Example 1 were added to a 500 cc. three necked round bottom flask fitted with a mechanical agitator, thermometer, dropping funnel, and a reflxu condenser with a vent for hydrogen chloride off-gas to a water absorber, said vent having a nitrogen purge on it. With the agitator on said silane starting material was heated to 55° C. at which point the dropwise addition of about 87.0 grams (0.65 moles) of sulfur monochloride (S$_2$Cl$_2$) via the dropping funnel was started. An exotherm was noted and the reaction temperature controlled at 55° C. by moderate cooling. After one hour all of the sulfur monochloride had been added. The reaction was maintained for about two hours at 55° C. at which time all hydrogen chloride gas evolution had essentially ceased. About 1.17 moles of hydrogen chloride were collected during said reaction period which indicates that the reaction product contains a small amount of polysulfurated product and possibly some tri and tetrapolysulfide linkages. The reflux condenser was then removed and replaced with a still head and a set of receivers designed to operate at 100 mm Hg. via a water aspirator system. The crude polysulfide reaction product which may be described as having the average formula $$[Cl_3-Si-C_2H_4-Ar]_2 [(S)_{2.83}]$$

wherein Ar is a tolylene radical was then vacuum esterified by treating it with about 200 grams (6.25 moles) of methanol (CH$_3$OH) at 60°-70° C. and about 150 mm Hg. Then about 40 cc. of toluene and about 5 grams of NaHCO$_3$ were added to the esterified product and slurried for about one-half hour to neutralize any residual acidity. The esterified polysulfide silane product was then pressure filtered and vacuum desolvated at about 125° C./0.1 mm Hg. and 0.075 moles (18.0 grams) of unsulfurated tolylethyltrimethoxysilane having a $n_d^{21}$ = 1.4830 were collected. A 94% yield of 247.5 grams of the desired methoxy esterified polysulfide silane product was obtained which had a $d^{21}$ = 1.5775. Elemental analysis of said desired product calculated as having the average formula $$[(CH_3O)_3-Si-C_2H_4-Ar]_2 [(S)_{2.83}]$$

wherein Ar is a tolylene radical showed:

| Element | Found | Calculated Average Formula |
|---|---|---|
| %C | 49.93 | 50.65 |
| %H | 6.26 | 6.68 |
| %Si | 10.20 | 9.85 |
| %S | 16.50 | 15.93 |

EXAMPLE 4

The sulfuration process of Example 3 was repeated using the same apparatus, reactants and conditions to produce a crude polysulfide reaction product which may be described as having the average formula

[Cl$_3$—Si—C$_2$H$_4$—Ar]$_2$ [(S)$_{2.83}$]

wherein Ar is a tolylene radical. The reflux condenser was then replaced with a still head and set of receivers as described in Example 3. With the agitator on about 35 grams of toluene were added to the reaction flask to reduce the viscosity of the crude polysulfide reaction product. The contents of the reaction flask were then degased by cautiously reducing the pressure to 100 mm Hg. The reaction system was then heated to 65°–70° C. and vacuum esterified at 100 mm Hg. absolute with about 300 grams (6.5) moles of anhydrous ethanol (C$_2$H$_5$OH) added via the dropping funnel over a two and one-half hour reaction period. The esterified polysulfide product was then neutralized with ten grams of NaHCO$_3$ for one-half hour at 60° C. to scavenge residual acidity. The neutralized product was then pressure filtered, the filter pad washed with 40 grams of toluene and the filtrates combined. The black colored liquid product was then vacuum desolvated at about 80° C./<0.1 mm Hg. and a 97.2% yield 318 grams of the desired ethoxy esterified polysulfide silane product was obtained which had a $n_d^{22.5} = 1.5380$ and a viscosity of about 250 centipoises at 22° C. Elemental analysis of said desired product calculated as having the average formula

[C$_2$H$_5$O$_3$—Si—C$_2$H$_4$—Ar]$_2$ [(S)$_{2.83}$]

wherein Ar is a tolylene radical showed:

| Element | Found | Calculated Average Formula |
|---|---|---|
| %C | 55.6 | 55.03 |
| %H | 7.76 | 7.64 |
| %Si | 9.0 | 8.56 |
| %S | 14.84 | 14.09 |

EXAMPLE 5

Using the same apparatus as described in Example 3, about 253.5 grams (1.0 mole) of the tolylethyltrichlorosilane product of Example 1, and about 1.3 grams of anhydrous FeCl$_3$ were added to the flask. While stirring said flask contents were heated to 55° C. and then about 67.5 grams (0.5 mole) of sulfur monochloride were added dropwise via the dropping funnel over about a one hour period while maintaining the reaction temperature at 50°–55° C. The reaction was continued at 50°–55° C. for about an additional one and one-half hour until hydrogen chloride gas evolution has essentially ceased. About 34 grams (0.93 moles) of hydrogen chloride were collected. The crude polysulfide reaction product which may be described as having the average formula

[Cl$_3$—Si—C$_2$H$_4$—Ar]$_2$[(S)$_{2.64}$]

wherein Ar is a tolylene radical was vacuum esterified by treating it with about 260 grams (8.14 moles) of methanol (CH$_3$OH) at 60°–70° C, and 125–200 mm Hg. absolute. The reflux condenser was then replaced with a still head and set of receivers as described in Example 3. Ten grams of NaHCO$_3$ were added to the esterified product which was slurried for one-half hour to neutralize any residual acidity. The esterified polysulfide silane product was then pressure filtered and the filter cake washed with toluene and the filtrate combined. Then the black colored product was vacuum desolvated at 125° c./<0.1 mm Hg. and 0.215 moles (51.6 grams) of unsulfurated tolylethyltrimethoxysilane having a $n_d^{20.5} = 1.4820$ were collected. A 98.9% yield (218.5 grams) of the desired methoxy esterified polysulfide silane product was obtained which had a $n_d^{20.5} = 1.5653$. Elemental analysis of said desired product calculated as having the average formula

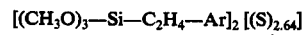
[(CH$_3$O)$_3$—Si—C$_2$H$_4$—Ar]$_2$ [(S)$_{2.64}$]

wherein Ar is a tolylene radical showed:

| Element | Found | Calculated Average Formula |
|---|---|---|
| %C | 50.7 | 51.2 |
| %H | 6.5 | 6.75 |
| %Si | 10.19 | 9.95 |
| %S | 15.46 | 15.02 |

EXAMPLE 6

Using the same apparatus as described in Example 3, about 253.5 grams (1.0 mole) of the tolylethyltrichlorosilane product of Example 1, and about 1.25 grams of anhydrous FeCl$_3$ were added to the flask. While stirring said flask contents were heated to 55° C. and then about 85.5 grams (0.65 mole) of sulfur monochloride were added dropwise via the dropping funnel over about a one hour period while maintaining the reaction temperature at 50°–55° C. The reaction was continued at 5°–55° C. for about an additional one and one-half hour until hydrogen chloride gas evolution had essentially ceased. The crude polysulfide reaction product which may be described as having the average formula

[Cl$_3$—Si—C$_2$H$_4$—Ar]$_2$ [(S)$_{2.83}$]

wherein Ar is a tolylene radical was vacuum esterified by treating it with about 260 grams (8.14 moles) of methanol at 60°–70° C. amd 125–200 mm Hg. absolute. The reflux condenser was then replace with a still head and set of receivers as described in Example 3. Ten grams of NaHCO$_3$ were added to the esterified product which was slurried for one-half hour to neutralize any residual acidity. The esterified polysulfide silane product was then pressure filtered and the filter cake washed with toluene and the filtrates combined. Then the black colored product was vacuum desolvated at 125° C./<0.1 mm Hg. and 18.0 grams of unsulfurated tolylethyltrimethoxysilane having a $n_d^{pf} = 1.4830$ were collected. A yield of about 247.5 grams of the desired methoxy esterified polysulfide silane product was obtained which had a $n_d^{20.5} = 1.5775$ refractive index. Elemental analysis of said desired product calculated as having the average formula

[(CH$_3$O)$_3$—Si—C$_2$H$_4$—Ar]$_2$ [(S)$_{2.83}$]

wherein Ar is a tolylene radical showed:

| Element | Found | Calculated Average Formula |
|---|---|---|
| %C | 49.93 | 50.65 |
| %H | 6.26 | 6.68 |
| %Si | 10.20 | 9.85 |

| Element | Found | Calculated Average Formula |
|---|---|---|
| %S | 16.5 | 15.93 |

EXAMPLE 7

Using the same apparatus as described in Example 3, about 239.5 grams (1.0 mole) of the phenylethyltrichlorosilane product of Example 2, and about 1.2 grams of anhydrous FeCl₃ were added to the flask. While stirring said flask contents were heated to 75° C. and then about 101.5 grams (0.75 mole) of the sulfur monochloride were added dropwise via the dropping funnel over about a two hour and 45 minute period while maintaining the reaction temperature at about 75° C. The reaction was allowed to continue overnight while maintaining the reaction temperature at about 75° C., during which period hydrogen chloride gas evolution had ceased. About 45.5 grams (1.24 moles) of hydrogen chloride were collected. The reflux condenser was then replaced with a still head and set of receivers as described in Example 3. The crude product mixture was then diluted with 75 grams of toluene and vacuum distilled at 100° C./<0.1 mm Hg. and about 33 grams of unsulfurated phenylethyltrichlorosilane were removed. The crude sulfurated chlorosilane product which may be described as having the average formula $$[Cl_3-Si-C_2H_4-Ar]_2 [(S)_{3.63}]$$

wherein Ar is a phenylene radical was then diluted with about 50 cc. of toluene and esterified with methanol at 60°-70° C. and 150–200 mm Hg. The esterified product was then neutralized with NaHCO₃ and pressure filtered. A 93.4% yield of about 228 grams of desired methoxy esterified polysulfide silane product was obtained which had a $n_d^{20.5}$ = 1.5848. Elemental analysis of said desired product calculated as having the average formula $$[(CH_3O)_3-Si-C_2H_4-Ar]_2 [(S)_{3.63}]$$

wherein Ar is a phenylene radical showed:

| Element | Found | Calculated Average Formula |
|---|---|---|
| %C | 47.01 | 46.64 |
| %H | 5.65 | 6.00 |
| %Si | 9.97 | 9.89 |
| %S | 20.66 | 20.49 |

EXAMPLE 8

Using the same apparatus as described in Example 3, about 239.5 grams (1.0 mole) of the phenlethyltrichlorosilane product of Example 2, and about 1.45 grams of anhydrous FeCl₃ were added to the flask. While stirring said flask contents were heated to 75° C. and then about 87.5 grams (0.65 mole) of sulfur monochloride were added dropwise via the dropping funnel over about a one hour period while maintaining the reaction temperature at about 75° C. The reaction was continued at about 75° C. for about an additional one hour and twenty minutes until hydrogen chloride gas evolution had essentially ceased. About 40 grams (1.1 moles) of hydrogen chloride were collected. The reflux condenser was then replaced with a still head and set of receivers as described in Example 3. The crude product mixture was then vacuum distilled at 95° C./<0.1 mm Hg. and about 0.215 moles (51.5 grams) of unsulfurated phenylethyltrichlorosilane were removed. No unreacted sulfur monochloride was found in the minus 80° C. traps protecting the vacuum system. The sulfurated chlorosilane product which may be described as having the average formula $$[Cl_3-Si-C_2H_4-Ar]_2 [(S)_{3.25}]$$

wherein Ar is a phenylene radical was then esterified with 250 grams (7.83 moles) of methanol at 50°-60° C. and 150 mm Hg. The esterified product was then neutralized with NaHCO₃ then pressure filtered and further heat treated at 95° C/0.1 mm Hg. A 94.3% yield (208 grams) of desired methoxy esterified polysulfide silane product was obtained which had a $n_d^{20.5}$ = 1.5836. Elemental analysis of said desired product calculated as having the average formula $$[(CH_3O)_3-Si-C_2H_4-Ar]_2 [(S)_{3.25}]$$

wherein Ar is a phenylene radical showed:

| Element | Found | Calculated Average Formula |
|---|---|---|
| %C | 47.06 | 47.65 |
| %H | 6.05 | 6.13 |
| %Si | 10.25 | 10.1 |
| %S | 19.06 | 18.8 |

EXAMPLE 9

Using the same apparatus as described in Example 3, about 239.5 grams (1.0 mole) of the phenylethyltrichlorosilane product of Example 2, and about 1.4 grams of anhydrous FeCl₃ were charged to the flask. While stirring said flask contents were heated to 75° C. and then about 67.5 grams (0.5 mole) of sulfur monochloride were added dropwise via the dropping funnel over about a one hour and twenty minute period while maintaining the reaction temperature at about 75° C. The reaction was continued at about 75° C. for about an additional one hour and twenty minute period until hydrogen chloride gas evolution had essentially ceased. The cruude sulfurated product mixture was then vacuum distilled at 95° C/0.1 mm Hg. and about 0.355 moles (85 grams) of unsulfurated phenylethyltrichlorosilane were removed. The reflux condenser was then replaced with a still head and set of receivers as described in Example 3. The crude sulfurated chlorosilane which may be depicted as having the average formula $$[Cl_3-Si-C_2H_4-Ar]_2 [(S)_{2.90}]$$

wherein Ar is a phenylene radical was then esterified with 7.8 moles (250 grams) of methanol at 50°-60° C./150 mm Hg. The esterified product was then neutralized with NaHCO₃, then pressure filtered and further heat treated at 95° C/0.2 mm Hg. A 98.3% yield (172 grams) of desired methoxy esterified polysulfide silane product was obtained which has a $n_d^{20.5}$ = 1.5728. Elemental analysis of said desired product calculated as having the formula $$[(CH_3O)_3-Si-C_2H_4-Ar]_2 [(S)_{2.90}]$$

wherein Ar is a phenylene radical showed:

| Element | Found | Calculated Average Formula |
|---|---|---|
| %C | 48.79 | 48.6 |
| %H | 6.33 | 6.26 |
| %Si | 10.2 | 10.3 |
| %S | 16.9 | 17.1 |

EXAMPLE 10

Example 9 was repeated except this time about 1.6 grams of anhydrous FeCl$_3$ and a reaction temperature of about 95° C. were employed. While the crude sulfurated product mixture was vacuum distilled at 100° C./<1.0 mm. Hg. and about 100.0 grams of unsulfurated phenylethyltrichlorosilane were removed. Upon esterifying with methanol, neutralizing the esterified product and filtering as described in Example 9, a 94.3% yield (156 grams) of desired methoxy esterified polysulfide silane product was obtained which had a $n_d^{20.5} = 1.5920$. Elemental analysis of said desired product calculated as having the average formula $$[(CH_3O)_3-Si-C_2H_4-Ar]_2[(S)_{3.71}]$$

wherein Ar is a phenylene radical showed:

| Element | Found | Calculated Average Formula |
|---|---|---|
| %C | 46.3 | 46.4 |
| %H | 5.72 | 5.97 |
| %Si | 10.16 | 9.85 |
| %S | 21.5 | 20.8 |

EXAMPLE 11

A series of vulcanized rubber compounds were prepared using the same cams curable rubber formulations and procedures wherein the amount and particular polysulfide silane compound employed was varied as shown in Table I. Polysulfide A represents the methoxy esterified polysulfide silane product of Example 5; Polysulfide B represents the methoxy esterified polyslfide silane product of Example 6 and Polysulfide C represents the ethoxy esterified polysulfide silane product of Example 4. The formulations in Table I were prepared in a laboratory banbury mixer utilizing full cooling water with a mix cycle of about 2½ to 3 minutes. The ingredients were added in the order listed, the polysulfide silane being added with the silica filler.

Table I

| Formulation | Control | A | B | C |
|---|---|---|---|---|
| Styrene butadiene Rubber[1] | 100 | 100 | 100 | 100 |
| Silica Filler[2] | 50 | 50 | 50 | 50 |
| Polysulfide A | — | 3.04 | — | — |
| Polysulfide B | — | — | 3.04 | — |
| Polysulfide C | — | — | — | 3.48 |
| Sundex 790 | 8 | 8 | 8 | 8 |
| Phenyl-alpha-naphthylamine | 1 | 1 | 1 | 1 |
| Flexamine G[4] | 1 | 1 | 1 | 1 |
| Zinc Oxide | 4 | 4 | 4 | 4 |
| Stearic acid | 1 | 1 | 1 | 1 |

[1]SBR1502
[2]A precipitated hydrated silica having an ultimate particle size of about 200 angstroms and containing about 87.5% SiO$_2$(Hi-Sil 210, Trademark of PPG Industries, Inc.)
[3]An aromatic processing oil (Trademark of Sun Oil Co.)
[4]A mixture containing about 65% of a complex diarylamine ketone reaction product and about 35% of N, N-diphenyl-p-phenylene diamine (Trademark of United States Rubber Co.)

After banbury mixing each formulation was catalyzed on a two roll mill by the addition of 1.5 parts of 2,2'-benzothiazole disulfide, 1.5 parts of di-orthotolylguanidine and 2.75 parts of sulfur. Each formulation was then vulcanized and the properties recorded as listed in Table II.

Table II

| Rubber Compounds | Control | A | B | C |
|---|---|---|---|---|
| Mooney Scorch at 275° F[1] | | | | |
| t5, MS 1 + (minutes) | 23 | 19 | 21 | 20 |
| Physical Properties (cured 10 min/320° F) | | | | |
| Hardness, Shore A[2] | 61 | 69 | 67 | 68 |
| Tensile Strength[3](psi) | 2430 | 2300 | 2250 | 2370 |
| Tear Strength, Die C[4] (ppi) | 169 | 292 | 251 | 258 |
| Modulus at 300% Elongation, (psi)[3] | 510 | 1460 | 1150 | 1380 |
| Goodrich Flexometer at 212° F, 17.5% compression, 143.5 psi static load, 20 minute condition time, 25 minute run, cured 15 min/320° F | | | | |
| Δ T, ° F[5] | 65 | 40 | 40 | 39 |
| Permanent Set, % | 15.0 | 5.6 | 6.1 | 5.1 |

[1]Tested in compliance with ASTM D-1646
[2]Tested in compliance with ASTM D-2240
[3]Tested in compliance with ASTM D-412
[4]Tested in compliance with ASTM D-624
[5]Tested in compliance with ASTM D-623, Method A This data demonstrates that all three polysulfide silane containing rubber compounds (A, B and C) when compared to the control compound without any polysulfide silane, exhibited superior stress-strain characteristics, tear strength, and reduced heat buildup during flexure, without unduly adversely affecting processing scorch safety; thus indicating that a more durable rubber article can be made by the addition of the polysulfide silanes of this invention without unduly sacrificing scorch safety.

EXAMPLE 12

A series of vulcanized rubber compounds were prepared using the same curable rubber formulations and procedures wherein the amount an particular polysulfide silane compound was varied as shown in Table III. Polysulfide A represents the methoxy esterified polysulfide silane product of Example 5; Polysulfide B represents the methoxy esterified polysulfide product of Example 6 and Polysulfide C represents the ethoxy esterified polysulfide silane product of Example 4. The formulations in Table III were prepared in a laboratory banbury mixer with full cooling water and a mix cycle of about 2 to 3 minutes. The ingredients were added in the order listed, the polysulfide silane being added with the clay filler.

Table III

| Formulation | Control | A | B | C |
|---|---|---|---|---|
| Neoprene W[1] | 100 | 100 | 100 | 100 |
| MgO dispersion[2] | 7.3 | 7.3 | 7.3 | 7.3 |
| Phenyl-alpha-naphthylamine | 2 | 2 | 2 | 2 |
| Lubricating polyethylene | 2 | 2 | 2 | 2 |
| Polysulfide A | — | 1.14 | — | — |
| Polysulfide B | — | — | 1.14 | — |
| Polysulfide C | — | — | — | 1.29 |
| Clay filler[3] | 100 | 100 | 100 | 100 |
| Naphthenic oil[4] | 15 | 15 | 15 | 15 |
| Zinc oxide | 5 | 5 | 5 | 5 |
| Stearic acid | 0.5 | 0.5 | 0.5 | 0.5 |

[1]Polychloroprene (Trademark of E.I. Dupont de Nemours)
[2]Maglite D-Bar (Trademark of Merck and Co.)
[3]Hydroglass, a hydrous aluminum silicate (Trademark of J.M. Huber Corp.)
[4]Circosol 4240 (Trademark of Sun Oil Co.)

After banbury mixing each formulation was catalyzed with 0.5 parts of tetramethylthiourea on a two roll mill.

Each formulation was then vulcanized and the properties recorded as listed in Table IV Table IV

| Rubber Compounds | Control | A | B | C |
|---|---|---|---|---|
| Mooney Scorch at 275° F[1] | | | | |
| ts MS 1 + minutes | 39 | 40 | 41 | 38 |
| Physical Properties (cured 45 min/320° F) | | | | |
| Hardness, Shore A[2] | 48 | 56 | 55 | 52 |
| Tensile Strength [3](psi) | 1760 | 2050 | 2020 | 1880 |
| Tear Strength, Die C[4], (ppi) | 146 | 280 | 286 | 239 |
| Modulus at 300% Elongation (psi)[3] | 270 | 870 | 820 | 630 |

[1]Tested in compliance with ASTM D-1646
[2]Tested in compliance with ASTM D-2240
[3]Tested in compliance with ASTM D-412
[4]Tested in compliance with ASTM D-624

This data demonstrates the improved stress-strain and tear properties obtained with utilization of the polysulfide silanes of this invvention while maintaining processing scorch safety.

EXAMPLE 13

A series of vulcanized rubber compounds were prepared using the same curable rubber formulations and procedures wherein the amount and particular polysulfide silane compound employed was varied as shown in Table V. Polysulfide D represents the methoxy esterified polysulfide silane product of Example 7, and Polysulfide E represents the methoxy exterified polysulfide silane product of Example 8. The formulations in Table V were prepared in a laboratory banbury mixer utilizing full cooling water and a mix cycle time of 2½ to 3 minutes. The ingredients were added in the order listed, the polysulfide silane being added with the silica filler.

Table V

| Formulation | Control | D | E |
|---|---|---|---|
| Styrene butadiene Rubber[1] | 100 | 100 | 100 |
| Silica Filler[2] | 501 | 50 | 50 |
| Polysulfide D | — | 1.44 | — |
| Polysulfide E | — | — | 1.44 |
| Sundex 790[3] | 8 | 8 | 8 |
| Phenyl-alpha-naphthylamine | 1 | 1 | 1 |
| Flexamine G[4] | 1 | 1 | 1 |
| Zinc oxide | 4 | 4 | 4 |
| Stearic acid | 1 | 1 | 1 |

[1]Same as defined in Table I
[2]Same as defined in Table I
[3]Same as defined in Table I
[4]Same as defined in Table I After banbury mixing each formulation was catalyzed on a two roll mill by the addition of 1.5 parts of 2,2'-benzothiazole disulfide, 1.5 parts of diorthotolylgandine and 2.75 parts of sulfur. Each formulation was then vulcanized and the properties recorded as listed in Table VI.

Table VI

| Rubber Compounds | Control | D | E |
|---|---|---|---|
| Mooney Scorch,[1]275° F | | | |
| t₅, MS 1 + (minutes) | 32 | 30 | 30 |
| Physical Properties (cured 15 min/320° F) | | | |
| Hardness Shore A[2] | 61 | 67 | 66 |
| Tensile Strength[3](psi) | 3050 | 2970 | 3110 |
| Tear Strength, Die C[4], (ppi) | 190 | 265 | 265 |
| Modulus at 300% Elongatio[3](psi) | 530 | 1040 | 1020 |
| Goodrich Flexometer at 212° F, 17.5% compression, 143.5 psi static load 20 minute condition time, 25 minute run, cured 20 min/320° F | | | |
| Δ T (° F)[5] | 73 | 51 | 54 |
| Permanent Set (%) | 14.3 | 6.1 | 6.3 |

[1]Tested in compliance with ASTM D-1646
[2]Tested in compliance with ASTM D-314
[3]Tested in compliance with ASTM D-412
[4]Tested in compliance with ASTM D-624
[5]Tested according to ASTM D-623, Method A This data demonstrates that both polysulfide containing rubber compounds (D and E) when compared to the control compound without any polysulfide silane give similar scorch times but greatly improved tear strength, stress-strain characteristics and reduced heat buildup during flexure; thus indicating that a more durable and servicable article can be made by the addition of the polysulfide silanes of this invention without an undue adverse effect on the processing characteristics (scorch) of such compounds.

EXAMPLE 14

A series of vulcanized rubber compounds were prepared using the same curable rubber formulations and procedures wherein the amount and particular polysulfide silane compound was varied as shown in Table VII. Polysulfide D represents the methoxy esterified polysulfide silane product of Example 7 and Polysulfide E represents the methoxy esterified polysulfide product of Example 8. The formulations in Table VII were prepared in a laboratory banbury mixer with full cooling water and a mix cycle of about 2 to 3 minutes. The ingredients were added in the order listed, the polysulfide silane being added with the clay filler.

Table VII

| Formulation | Control | D | E |
|---|---|---|---|
| Neoprene W[1] | 100 | 100 | 100 |
| MgO dispersion[2] | 7.3 | 7.3 | 7.3 |
| Phenyl-alpha-naphthylamine | 2 | 2 | 2 |
| Lubricating polyethylene | 2 | 2 | 2 |
| Polysulfide D | — | 1.08 | — |
| Polysulfide E | — | — | 1.08 |
| Clay filler[3] | 100 | 100 | 100 |
| Naphthenic Oil[4] | 15 | 15 | 15 |
| Zinc Oxide | 5 | 5 | 5 |
| Stearic Acid | 0.5 | 0.5 | 0.5 |

[1]Same as defined in Table III
[2]Same as defined in Table III
[3]Same as defined in Table III
[4]Same as defined in Table III After banbury mixing each formulation was catalyzed with 0.5 parts of tetramethylthiourea on a two roll mill. Each formulation was then vulcanized and the properties recorded as listed in Table VIII.

Table VIII

| Rubber Compounds | Control | D | E |
|---|---|---|---|
| Mooney Scorch[1], 275° F | | | |
| t₁₀, MS 1 + (minutes) | 44 | 37 | 42 |
| Physical Properties (cured 45 min/307° F) | | | |
| Hardness Shore A[2] | 48 | 53 | 55 |
| Tensile Strength[3](psi) | 1900 | 2100 | 2180 |
| Tear Strength, Die C[4] (ppi) | 190 | 325 | 330 |
| Modulus at 300% elong- | | | |

Table VIII-continued

| Rubber Compounds | Control | D | E |
|---|---|---|---|
| ation³(psi) | 410 | 1100 | 1110 |

[1]Tested in compliance with ASTM D-1646
[2]Tested in compliance with ASTM D-314
[3]Tested in compliance wih ASTM D-412
[4]Tested in compliance with ASTM D-624

This data demonstrates the improved stress-strain and tear properties obtained with utilization of the polysulfide silanes of this invention with only a minor decrease in scorch time.

EXAMPLE 15

About 239.5 grams (1.0 mole) of phenylethyltrichlorosilane and about 0.31 grams of anhydrous $FeCl_3$ were charged to a 500 cc., three necked round bottom flask fitted with a mechanical stirrer, thermometer dropping funnel and reflux condenser which was vented to a hood via a bubbler. While stirring the flask contents were heated to 90° C and over a two and one-half hour period about 67.5 grams (0.5 mole) of sulfur monochloride were added dropwise via the dropping funnel while maintaining the reaction temperature at about 90° C. The reaction was allowed to continue at about 90° C for an additional four hours during which time the evolution of hydrogen chloride had ceased. About 150 ml. of toluene and about 10 grams of activated carbon were then added to the crude sulfurated silane product and the mixture filtered to give a clear dark brown solution. The sulfurated chlorosilane product was converted to the methoxy ester by a 28 hour treatment with excess trimethyl orthoformate. Residual traces of chloride were neutralized by treatment with small amounts of propylene oxide. Excess trimethyl orthoformate was removed and the toluene concentration adjusted to give a solution comprising 60 percent of the methoxy esterified polysulfide silane and 40 percent toluene. Then about 150 cc. of crude methoxy esterified polysulfide silane/toluene solution was then charged to a 300 ml. stainless steel rocking autoclave along with about 3 grams of cobalt sulfide catalyst. The system was flushed with nitrogen, then pressurized with hydrogen to 1500 psig. at room temperature and the autoclave rocked for four hours at 180° C until no further absorption of $H_2$ gas was observed. The contents were then discharged from the cooled autoclave and vacuum distilled at about 0.1 mm Hg. A yield of about 0.124 moles (35 grams) (constant boiling fraction at 95° C/0.1 mm Hg.) of the desired methoxy esterified silane mercaptan product was obtained and had a $n_d^{23} = 1.5174$. Nuclear magnetic resonance absorption analysis of said silane mercaptan product was consistent for an isomeric mixture of $(CH_3O)_3SiCH_2CH_2ArSH$ and

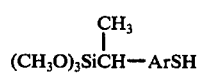

wherein Ar is phenylene. Elemental analysis of said desired silane mercaptan product calculated as having the average formula $(CH_3O)_3SiC_2H_4ArSH$ wherein Ar is phenylene showed:

| Element | Found | Calculated Average Formula |
|---|---|---|
| %C | 51.37 | 51.11 |
| %H | 6.93 | 6.97 |
| %Si | 11.04 | 10.86 |
| %S | 12.18 | 12.41 |

EXAMPLE 16

Two vulcanized rubber compounds were prepared by mixing the ingredients listed below on a two roll mill whose initial temperature was 120°-130° F. The rubber polymer was banded, part of the filler and all of the silane added, then the balance of the filler and plasticizer added followed by the curatives. Silane F represents the methoxy esterified silane mercaptan product of Example 15.

Table IX

| Formulation | Control | F |
|---|---|---|
| NBR[1] | 100 | 100 |
| Silica Filler[2] | 50 | 50 |
| Silane F | — | 0.4 |
| Di-(2-ethylhexyl) azelate[3] | 10 | 10 |
| Zinc Oxide | 5 | 5 |
| Stearic Acid | 0.5 | 0.5 |
| 2,2'Benzothiazole Disulfide | 2 | 2 |
| Tetra Methyl Thiuram Disulfide | 1 | 1 |
| Sulfur | 0.3 | 0.3 |

[1]Chemigum N615, a nitrile polybutadiene rubber (Trademark of Goodyear Tire and Rubber Co.)
[2]A precipitated hydrated silica filler (HiSil 233, Trademark of PGG Industries, Inc.
[3]A plasticizer, $C_7H_{14}[COOCH_2CH(C_2H_5)C_4H_9]_2$ Each formulation was vulcanized for 90 minutes at 310° F. and the properties recorded as listed in Table X.

Table X

| Rubber Compounds | Control | F |
|---|---|---|
| Hardness, Shore A[1] | 66 | 66 |
| Tensile Strength[2] (psi) | 2700 | 2540 |
| Tear Strength, Die[3] C (ppi) | 324 | 305 |
| Set at break[2] (%) | 50 | 35 |
| Elongation[2](%) | 930 | 700 |
| Modulus at 300% elongation[2], (psi) | 470 | 840 |

[1]Tested in compliance with ASTM D-314
[2]Tested in compliance with ASTM D-412
[3]Tested in compliance with ASTM D-624

The data demonstrates that the silane mercaptan containing rubber compound (F) when compared to the control compound without any silane mercaptan exhibited a vastly superior modulus value indicating that such rubbers will possess improved dynamic physical properties such as abrasion resistance, and the like.

EXAMPLE 17

About 264.5 grams (1.25 moles) of phenyltrichlorosilane and about 1.45 grams of anhydrous $FeCl_3$ were added to a 500 cc. three necked round bottom flask fitted with a mechanical agitator dropping funnel, thermometer and reflux condenser whose vent lead to a hydrogen chloride absorber. While stirring the flask contents were heated to 100° C. and 110 grams (0.815) mole) of sulfur monochloride were added dropwise via the dropping funnel over a two hour and fifteen minute period while maintaining the reaction temperature at about 100° C. The reaction condition was continued at about 95° C. for an additional 16 hours until hydrogen gas evolution had ceased. The crude polysulfide reaction product which may be described as having the average formula

[Cl₃—Si—Ar]₂[(S)₃.₀₇]

wherein Ar is a phenylene radical was vacuum esterified with an excess of methanol at 65°-75° C/125-150 mm Hg. The reflux condenser was then replaced with a still head and set of receivers as described in Example 3. The crude esterified product was then diluted with about 100 cc. of toluene, neutralized with NaHCO₃ and decolorizing charcoal and then pressure filtered. The clear filtrate product was then vacuum desolvated at about 90° C/0.1 mm Hg. and about 0.018 moles (3.5 grams) of unsulfurated phenyltrimethoxysilane having a boiling point of 50° C/1.0 mm Hg. was removed. Elemental analysis of the black viscous methoxy esterified polysulfide silane product calculated as having the average formula

[(CH₃O)₃—Si—Ar]₂ [(S)₃.₀₇]

wherein Ar is a phenylene radical showed;

| Element | Found | Calculated Average Formula |
|---------|-------|---------------------------|
| %C | 42.59 | 43.9 |
| %H | 4.7 | 5.3 |
| %Si | 11.9 | 11.37 |
| %S | 20.87 | 19.95 |

EXAMPLE 18

Using the same apparatus as described in Example 17, about 169 grams (0.75 mole) of tolyltrichlorosilane and 0.95 grams of anhydrous FeCl₃ were charged to the flask. While stirring said flask contents were heated to 80° C. and then about 50.6 grams (0.375 mole) of sulfur monochloride were added dropwise in the dropping funnel over a two and one-half hour period while maintaining the reaction temperature at about 80° C. The reaction was continued at about 80° C for an additional 17 hours and 30 minutes at which point hydrogen chloride gas evolution had ceased. About 0.71 moles (26 grams) of hydrogen chloride were collected in the absorber. The crude polysulfide reaction product which may be described as having the average formula

[Cl₃—Si—Ar]₂ [(S)₂.₆₅]

wherein Ar is a tolylene radical was vacuum esterified with an excess of methanol at 65° C/125 mm Hg. The reflux condenser was then replaced with a still head and set of receivers as described in Example 3. The crude esterified product was then neutralized with NaHCO₃, pressure filtered and vacuum desolvated at about 90° C/0.1 mm Hg. and about 0.024 moles (5.1 grams) of unsulfurated tolyltrimethoxysilane was collected having a boiling point of about 55° C/0.05 mm Hg., a $n_d^{23.5}$ = 1.4726 and which was identified by nuclear magnetic resonance. Elemental analysis of the black methoxy esterified polysulfide silane product calculated as having the average formuls

[(MeO)₃Si—Ar]₂ [(S)₂.₆₅]

wherein Ar is a tolylene radical showed:

| Element | Found | Calculated Average Formula |
|---------|-------|---------------------------|
| %C | 47.7 | 47.35 |

| Element | Found | Calculated Average Formula |
|---------|-------|---------------------------|
| %H | 5.83 | 5.92 |
| %S | 16.8 | 16.73 |
| %Si | 11.1 | 11.05 |

EXAMPLE 19

About 254 pounds (1 lb. mole) of tolylethyltrichlorosilane and about 1150 grams of TiCl₄ were charged to a 50 gallon pilot scale glass lined reactor equipped with a mechanical agitator, a vented condenser system leading to a hydrogen chloride scrubber, recording themocouple, a controlling heat transfer system designed to heat or cool and an auxiliary liquid feed tank, the entire reactor system having the capability of operating at reduced pressure and super atmospheric pressure. Said reactor contents were then heated to 90° C. with agitation and about 87 pounds (0.5 lb. mole) of sulfur monochloride slowly and continuously added via the auxilliary feed tank while the reaction temperature was maintained at about 90° C. During said addition of the sulfur monochloride a steady stream of hydrogen chloride gas was released and absorbed in the scrubber. The evolution of hydrogen chloride creases inside of one hour after addition of all of the sulfur monochloride. The crude polysulfide reaction kettle product which may be described as having the average formuls

[Cl₃—Si—C₂H₄—Ar]₂[(S)₂.₉₈]

wherein Ar is a tolylene radical was then esterified by the following atmospheric pressure procedures: About 40 pounds of toluene was added to the reaction kettle. The kettle contents were heated to 85° C. and about 300 pounds (6.5 lb. moles) of anhydrous ethanol slowly added. The hydrogen chloride by-product from esterification was absorbed in the scrubber. The reaction kettle temperature was gradually increased to 100° C. Any trace of residual acidity was neutralized by stirring with about five pounds of propylene oxide. The esterified polysulfide silane reaction product was then heated at about 125° C and 150 mm Hg. pressure to remove all traces of unreacted propylene oxide, ethanol and toluene. The filtered black liquid desired ethoxy esterified polysulfide silane product 0.39 lb. moles (about 256 pounds) had a $n_d^{22.5}$=1.5308 and a viscosity of about 21.4 centistokes at 25° C. Elemental analysis of said desired product calculated as having the average formula

[(C₂H₅O)₃—Si—C₂H₄—Ar]₂ [(S)₂.₉ₐ]

wherein Ar is a tolylene radical showed:

| Element | Found | Calculated Average Formula |
|---------|-------|---------------------------|
| %C | 55.6 | 54.75 |
| %H | 7.55 | 7.60 |
| %S | 14.5 | 14.52 |
| %Si | 8.5 | 8.51 |

EXAMPLE 20

A series of vulcanized rubber compounds were prepared using the same curable rubber formulations and procedures wherein the amount and particular polysulfide silane compound employed was varied as shown in Table XI. Polysulfide G represents the methoxy esterified polysulfide silane product of Example 17; and Polysulfide H represents the methoxy esterified polysulfide silane product of Example 18. The formulations in Table XI were prepared in a laboratory banbury mixer utilizing full cooling water wih a mix cycle of about 2½ to 3 minutes. The ingredients were added in the order listed, the polysulfide silane being added with the silica filler.

Table XI

| Formulation | Control | G | H |
|---|---|---|---|
| Styrene Butadiene Rubber[1] | 96.3 | 96.3 | 96.3 |
| Cis-1,4-Polybutadiene[2] | 30 | 30 | 30 |
| Silica Filler[3] | 70 | 70 | 70 |
| Polysulfide G | — | 3.5 | — |
| Polysulfide H | — | — | 3.5 |
| Sundex 790[4] | 10 | 10 | 10 |
| Zinc Oxide | 4 | 4 | 4 |
| Stearic acid | 1 | 1 | 1 |

[1]SBR 1712
[2]Budene 1207 (Trademark of Goodyear Tire and Rubber Co.)
[3]Precipitated silica, (Hil-Sil 233, Trademark of PPG Industries, Inc.)
[4]An aromatic processing oil (Trademark of Sun Oil Co.)

After banbury mixing each formulation was catalyzed on a two roll mill by the addition of 0.2 parts of tetramethyl thiuram monosulfide, 1.2 parts of N-tert-butyl-2-benzothiazolesulfenamide, 2.5 parts of di-orthotolyl-guanidine, and 1.6 parts of sulfur. Each formulation was then vulcanized and the properties recorded as listed in Table XII.

Table XII

| Rubber Compounds | Control | G | H |
|---|---|---|---|
| Mooney Scorth at 275° F[1] | | | |
| t5 MS 1+ (minutes) | 26 | 24 | 24 |
| Physical Properties (cured 10 min/320° F) | | | |
| Hardness, Shore A[2] | 51 | 52 | 52 |
| Tensile Strength[3] (psi) | 2450 | 2880 | 2860 |
| Tear Strength, Die C[4] (ppi) | 181 | 234 | 229 |
| Modulus at 300% | 280 | 500 | 540 |
| Elongation, (psi)[3] | | | |

[1]Tested in compliance with ASTM D-1646
[2]Tested in compliance with ASTM D-2240
[3]Tested in compliance with ASTM D-412
[4]Tested in compliance with ASTM D-624

This data demonstrates that both polysulfide silane containing rubber compounds (G and H) when compared to the control compound without any polysulfide silane, exhibited superior stress-strain characteristics and tear strength, without unduly adversely affecting processing scorch safety; thus indicating that a more durable rubber article can be made by the addition of the polysulfide silanes of this invention without unduly sacrificing scorch saftey.

EXAMPLE 21

About 167 pounds (0.66 lb.-mole) of tolylethyltrichlorosilane and about 800 grams (1 pint) of TiCl₄ were charged to a 50 gallon pilot scale glass lined reactor equipped with a mechanical agitator, a vented condenser system leading to a hydrogen chloride scrubber, recording themocouple, a controlling heat transfer system designed to heat or cool and an auxilliary liquid feed tank, the entire reactor system having the capability of operating at reduced pressure and super atmospheric pressure. Said reactor contents were then heated to 90° C. with agitation and about 47 pounds (0.35 lb.-mole) of sulfur monochloride slowly and continuously added via the auxilliary feed tank over three hours while the reaction temperature was maintained at about 90° C. During said addition of the sulfur monochloride a steady stream of hydrogen chloride gas was released and absorbed in the scrubber. The reaction was maintained for an additional two hours at about 90° C., the evolution of hydrogen chloride having ceased at about one hour after addition of all of the sulfur monochloride. The crude polysulfide reaction kettle product which may be described as having the average formula

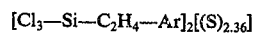
[Cl₃—Si—C₂H₄—Ar]₂[(S)₂.₃₆]

wherein Ar is a tolylene radical was then esterified by the following atmospheric pressure procedure: About 2 gallons of xylene were added to the reaction kettle. The kettle contents were heated to 85° C. and about 16 gallons of anhydrous ethanol slowly added. The hydrogen chloride by-product from esterification was absorbed in the scrubber. The reaction kettle temperature was gradually increased to 100° C. Any trace of residual acidity was neutralized by stirring with about five pounds of propylene oxide. The esterified polysulfide silane reaction product was then heated at about 125° C and 150 mm Hg pressure to remove all traces of unreacted propylene oxide, ethanol and xylene. The filtered black liquid desired ethoxy esterified polysulfide silane product (about 182 pounds) had a $n_d^{25}$ = 1.5240, a specific gravity of 1.084 and a viscosity of 40.2 centistokes at 25° C. Elemental analysis of said desired product calculated as having the average formula
[(C₂H₄O)₃—Si—C₂H₄—Ar]₂[(S)₂.₃₆]

wherein Ar is a tolylene radical showed:

| Element | Found | Calculated Average Formula |
|---|---|---|
| %C | 57.04 | 56.4 |
| %H | 7.59 | 7.84 |
| %S | 11.36 | 11.87 |
| %Si | 8.41 | 8.78 |

EXAMPLE 22

About 167 pounds (0.66 lb.-mole) of tolylethyltrichlorosilane and about 800 grams (1 pint) of TiCl₄ were charged to a 50 gallon pilot scale glass lined reactor equipped with a mechanical agitator, a vented condenser system leading to a hydrogen chloride scrubber, recording themocouple, a controlling heat transfer system designed to heat or cool and an auxilliary liquid feed tank, the entire reactor system having the capability of operating at reduced pressure and super atmospheric pressure. Said reactor contents were then heated to 90° C. with agitation and about 92 pounds (0.68 lb.-mole) of sulfur monochloride slowly and continuously added via the auxilliary feed tank over three hours while the reaction temperature was maintained at about 90° C. During said addition of the sulfur monochloride a steady stream of hydrogen chloride gas was released and absorbed in the scrubber. The reaction was maintained for an additional two hours at about 90° C., the evolution of hydrogen chloride having ceased at about one hour after addition of all of the sulfur monochloride. The crude polysulfuration reaction product was then esterified by the following atmospheric pressure procedure: About 2 gallons of xylene were added to the reaction kettle. The kettle contents were heated to 85° C. and about 16 gallons of anhydrous ethanol slowly added. The hydrogen chloride by-product from esterification was absorbed in the scrubber. The reaction kettle temperature was gradually increased to 100° C. Any trace of residual acidity was neutralized by stirring with about five pounds of propylene oxide. The esterified polysulfide silane reaction product was then heated at about 125° C. and 150 mm Hg pressure to remove all traces of unreacted propylene oxide, ethanol, and xylene. The filtered black liquid desired ethoxy esterified polysulfide silane product (about 216 pounds) had a $n_d{}^{25} = 1.5323$ and a viscosity of about 450 centistokes at 25° C. The high viscosity of the ethoxy esterified polysulfide silane product indicates the presence of two polysulfide bridging groups each bonded to different carbon atoms of the same aryl radical. Elemental analysis of said desired product calculated as having empirical formula $C_{30}H_{48}O_6Si_2S_4$

| Element | Found | Calculated Average Formula |
|---|---|---|
| %C | 52.5 | 52.3 |
| %H | 7.20 | 6.98 |
| %S | 17.8 | 18.6 |
| %Si | 7.71 | 8.13 |

EXAMPLE 23

Twenty-three grams of a polysulfurated tolylethyl triethoxysilane product prepared according to the procedure of Example 4 was poured into a Teflon lined pan to a height of about 1/8–1/16 of an inch and allowed to stand at room temperature overnight. The liquid polysulfide product was found to have solidified overnight which is considered to have been caused by hydrolysis and condensation of the polysulfide produce because of the moisture in the air. The solid polysulfide product was broken into chunks and used to prepare a vulcanized rubber compound. A control vulcanized rubber compound was also prepared using the same procedure and curable rubber formulation as shown in Table XIII. Polysulfide K represents said solid polysulfide product in chunk form. The formulations in Table XIII were prepared in a laboratory banbury mixture utilizing full cooling water with a mix cycle of about 2½ to 3 minutes. The ingredients were added in the order listed, the polysulfide product being added with the silica filler.

TABLE XIII

| Formulation | Control | K |
|---|---|---|
| Styrene butadiene Rubber[1] | 100 | 100 |
| Silica Filler[2] | 50 | 50 |
| Polysulfide K | — | 3.5 |
| Sundex 790[3] | 8 | 8 |
| Phenyl-alpha-naphthylamine | 1 | 1 |
| Flexamine G[4] | 1 | 1 |
| Zinc Oxide | 4 | 4 |
| Stearic acid | 1 | 1 |

[1]Same as defined in Table I
[2]Same as defined in Table I
[3]Same as defined in Table I
[4]Same as defined in Table I After banbury mixing both formulations were catalyzed on a two roll mill by the addition of 1.5 parts of 2,2'-benzothiazole disulfide, 1.5 parts of di-orthotolylguanidine and 2.75 parts of sulfur. Both formulations were then vulcanized and the properties recorded as listed in Table XIV.

TABLE XIV

| Rubber Compounds | Control | K |
|---|---|---|
| Mooney Scorch at 275° F | | |
| t5, MS 1 + (minutes) | 24 | 22 |
| Physical Properties (Cured 10 min./320° F) | | |
| Hardness, Shore A[2] | 59 | 62 |
| Tensile Strength[3](psi) | 2450 | 1510 |
| Tear Strength, Die C[4] (ppi) | 197 | 205 |
| Modulus at 300% Elongation, (psi)[3] | 640 | 800 |

[2]Tested in compliance with ASTM D-2240
[3]Tested in compliance with ASTM D-412
[4]Tested in compliance with ASTM D-624

The above data demonstrates that the polysulfide containing rubber compound product exhibited superior modulus over that of the control rubber compound, indicating that reduced heat buildup during flexure can be obtained using the polysulfide compounds of the instant invention. It is considered that the low tensile strength of the polysulfide containing rubber compound was due to using the solid polysulfide in chunk form which was not adequately dispersed throughout the rubber thus causing the premature tensile rupture.

Various modifications and variations of this invention will be obvious to a worker skilled in the art and it is to be understood that such modifications and variations are to be included within the purview of this application and the spirit and scope of the appended claims.

What is claimed is:

1. A polysulfide aryl silane compound having the average formula $$\left[ X_{3-y} - \underset{\underset{R'_y}{|}}{Si} - (R)_n - Ar \right]_a [(S)_x]_b$$

wherein X is a hydrolyzable group selected from the class consisting of halogen, alkoxy and acyloxy radicals; R' is an alkyl radical containing from 1 to 4 carbon atoms; y has a value of 0 to 2 inclusive; R is a divalent bridging group selected from the class consisting of alkylene and alkyleneoxy, radicals containing from 1 to 7 carbon atoms; n has a value of 0 or 1; Ar is an aryl radical containing from 6 to 12 carbon atoms; (S)$_x$ is a divalent polysulfide radical each free valence thereof being directly bonded to an aromatic carbon atom of an Ar radical whereby each Ar radical is bonded to another Ar radical through a (S)$_x$ radical, x has a value of from 2 to 6; a has a value of at least 2; b has a value of at least 1; and wherein the ratio of a to b is a value ranging from 0.4 to 2; and hydrolyzates and condensates thereof.

2. A polysulfide aryl silane compound as defined in claim 1, wherein y is 0; n is 0; Ar is an aryl radical selected from the group consisting of phenyl, an alkyl substituted phenyl radical wherein said alkyl radical contains from 1 to 4 carbon atoms and an alkoxy substituted phenyl radical wherein said alkoxy radical contains from 1 to 4 carbon atoms; and wherein the ratio of a to b is a value ranging from 0.6 to 2.

3. A polysulfide aryl silane compound as defined in claim 2, wherein X is chlorine and Ar is selected from the group consisting of phenyl and tolyl radicals.

4. A polysulfide aryl silane compound as defined in claim 2, wherein X is selected from the group consisting of methoxy and ethoxy radicals and Ar is selected from the group consisting of phenyl and tolyl radicals.

5. A polysulfide aryl silane compound as defined in claim 1, wherein $y$ is 0; $n$ is 1; R is a divalent alkylene radical having from 2 to 4 carbon atoms; and wherein Ar is an aryl radical selected from the group consisting of phenyl, an alkyl substituted phenyl radical wherein said alkyl radical contains from 1 to 4 carbon atoms and an alkoxy substituted phenyl radical wherein said alkoxy radical contains from 1 to 4 carbon atoms.

6. A polysulfide aryl silane compound as defined in claim 1, wherein $a$ is 2 and $b$ is 1.

7. A polysulfide aryl silane compound as defined in claim 5, wherein X is chlorine; Ar is selected from the group consisting of phenyl and tolyl radicals; and wherein R is a $-C_2H_4-$ radical.

8. A polysulfide aryl silane compound as defined in claim 7, wherein $a$ is 2 and $b$ is 1.

9. A polysulfide aryl silane compound as defined in claim 5, wherein X is selected from the group consisting of methoxy and ethoxy radicals; Ar is selected from the group consisting of phenyl and tolyl radicals; and wherein R is a $-C_2H_4$ radical.

10. A polysulfide aryl silane compound as defined in claim 9, wherein $a$ is 2 and $b$ is 1.

11. A process for preparing a polysulfide aryl halo-containing silane compound having the average formula

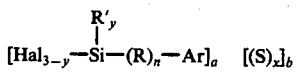

wherein Hal is a halogen atom; R' is an alkyl radical containing from 1 to 4 carbon atoms; $y$ has a value of 0 to 2 inclusive; R is a divalent bridging group selected from the class consisting of alkylene and alkyleneoxy radicals containing from 1 to 7 carbon atoms; $n$ has a value of 0 or 1; Ar is a aryl radical containing from 6 to 12 carbon atoms; $(S)_x$ is a divalent polysulfide radical each free valence thereof being directly bonded to an aromatic carbon atom of an Ar radical whereby each Ar radical is bonded to another Ar radical through a $(S)_x$ radical; $x$ has a value of from 2 to 6; $a$ has a value of at least 2; $b$ has a value of at least 1; and wherein the ratio of $a$ to $b$ is a value ranging from 0.4 to 2; said process comprising reacting (a) an arylhalosilane having the formula

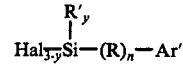

wherein Hal, R, R', $y$ and $n$ are the same as defined above and wherein Ar' represents a monovalent aryl radical containing from 6 to 12 carbon atoms with (b) sulfur monochloride, at least one mole of sulfur monochloride being employed for every two moles of aryl halosilane starting material used, and maintaining the reaction until hydrogen halide gas evolution has essentially ceased.

12. A process as defined in claim 11, wherein from 1 to about 4 moles of sulfur monochloride are employed for every two moles of aryl halosilane starting material used and wherein said process is carried out in the presence of a Lewis acid catalyst.

13. A process as defined in claim 12, wherein the catalyst is selected from the group consisting of $FeCl_3$ and $TiCl_4$.

14. A process as defined in claim 13, wherein $y$ is 0; $n$ is 0; Hal is chlorine; Ar is an aryl radical selected from the group consisting of phenyl and tolyl radicals; and Ar' is a monovalent aryl radical selected from the group consisting of phenyl and tolyl radicals.

15. A process as defined in claim 13 wherein $y$ is 0; $n$ is 1; Hal is chlorine; R is a divalent alkylene radical containing from 2 to 4 carbon atoms; Ar is an aryl radical selected from the group consisting of phenyl and tolyl radicals; and Ar' is a monovalent aryl radical selected from the group consisting of phenyl and tolyl radicals.

16. A process as defined in claim 15, wherein R' is a $-C_2H_4-$ radical.

17. A process as defined in claim 12, wherein from about 1 to about 1.5 moles of sulfur monochloride are employed for every two moles of aryl halosilane starting material used.

* * * * *